United States Patent
Sanderson et al.

(10) Patent No.: US 11,326,216 B2
(45) Date of Patent: May 10, 2022

(54) PROCESS FOR HYDROLYSIS OF OLIGOSACCHARIDES

(71) Applicant: Renmatix, Inc., King of Prussia, PA (US)

(72) Inventors: Charles Sebastian Sanderson, Wayne, PA (US); Daniel Roger Beacom, Wayne, PA (US)

(73) Assignee: Renmatix, Inc., King of Prussia, PA (US)

( * ) Notice: Subject to any disclaimer, the term of this patent is extended or adjusted under 35 U.S.C. 154(b) by 252 days.

(21) Appl. No.: 16/650,375

(22) PCT Filed: Sep. 26, 2018

(86) PCT No.: PCT/US2018/052966
§ 371 (c)(1),
(2) Date: Mar. 24, 2020

(87) PCT Pub. No.: WO2019/067624
PCT Pub. Date: Apr. 4, 2019

(65) Prior Publication Data
US 2020/0291492 A1    Sep. 17, 2020

Related U.S. Application Data

(60) Provisional application No. 62/563,212, filed on Sep. 26, 2017.

(51) Int. Cl.
*C13K 1/02*    (2006.01)
(52) U.S. Cl.
CPC ..................................... *C13K 1/02* (2013.01)
(58) Field of Classification Search
None
See application file for complete search history.

(56) References Cited

U.S. PATENT DOCUMENTS

| | | | | |
|---|---|---|---|---|
| 4,036,694 A | * | 7/1977 | Meguro | C13B 20/02 |
| | | | | 435/100 |
| 4,254,227 A | * | 3/1981 | Okada | C12P 19/18 |
| | | | | 435/97 |

(Continued)

FOREIGN PATENT DOCUMENTS

JP    10-327900 A2    12/1998
WO    WO 2019/067624    4/2019

OTHER PUBLICATIONS

International Search Report and Written Opinion dated Apr. 4, 2019 by the International Searching Authority for International Application No. PCT/US2018/052966, filed on Sep. 26, 2018 and published as WO 2019/067624 on May 23, 2019 (Applicant—Renmatix, Inc) (13 Pages).

(Continued)

*Primary Examiner* — Stefanie J Cohen
(74) *Attorney, Agent, or Firm* — Ballard Spahr LLP; Brian Shortell; Paul R. Darkes

(57) ABSTRACT

Provided is a method comprising (a) providing a hydrolysis composition of at least 20 wt % of sugar equivalents, wherein the hydrolysis composition comprises a first oligosaccharide, water, optionally a soluble aromatic compound, (b) contacting the hydrolysis composition with a catalyst in a first reactor to hydrolyze at least a portion of the first oligosaccharide to form a first product composition comprising a first monosaccharide and a second oligosaccharide, (c) separating the first monosaccharide from the first product composition to form a second product composition comprising the second oligosaccharide, wherein at least a portion of the second oligosaccharide is a reversion sugar, and (d) converting via a further hydrolysis step at least a portion of the second oligosaccharide to form a third product composition comprising a second monosaccharide.

6 Claims, 7 Drawing Sheets

(56) References Cited

U.S. PATENT DOCUMENTS

| | | |
|---|---|---|
| 2004/0198965 A1 | 10/2004 | Mollee et al. |
| 2011/0287493 A1 | 11/2011 | Marzialetti et al. |
| 2012/0232264 A1 | 9/2012 | Sato et al. |
| 2012/0247763 A1* | 10/2012 | Rakitsky ............... C09K 8/506 166/279 |
| 2014/0288298 A1 | 9/2014 | Nakagame et al. |

OTHER PUBLICATIONS

International Preliminary Report on Patentability dated Mar. 31, 2020 by the International Searching Authority for International Application No. PCT/US2018/052966, filed on Sep. 26, 2018 and published as WO 2019/067624 on May 23, 2019 (Applicant—Renmatix, Inc) (6 Pages).

* cited by examiner

PROCESS FOR HYDROLYSIS OF OLIGOSACCHARIDES

CROSS-REFERENCE TO RELATED APPLICATIONS

This Application is a U.S. National Phase of International Application No. PCT/US2018/052966, filed Sep. 26, 2018, which claims priority to U.S. Provisional Application No. 62/563,212, filed Sep. 26, 2017, the contents of which are incorporated herein by reference in their entireties.

BACKGROUND OF THE INVENTION

Lignocellulosic feedstocks primarily comprise cellulose, hemicelluloses, and lignin. Lignocellulosic feedstocks typically are obtained from renewable resources, such as agriculture, forests, and refineries associated therewith and are not considered to be food sources. In view of these aspects, lignocellulosic feedstocks are considered desirable for the production of biofuels, chemicals, and polymers. In particular, biofuels, such as ethanol and butanol, typically are produced from a lignocellulosic feedstock through a process of fermentation of saccharides, particularly monosaccharides.

During the hydrolysis of a lignocellulosic feedstock, oligosaccharides are formed (herein, an original oligosaccharide composition) that can be further broken down via hydrolysis (most commonly, an acid-catalyzed hydrolysis) to form monosaccharides. The monosaccharides are the feedstock for the fermentation or catalytic process to form biofuels, chemicals, and other fermentation or catalysis products. However, the hydrolysis process produces some by-products that are fermentation inhibitors. A process called overliming is known to reduce the concentration of hydroxymethyl furfural (HMF) and other fermentation, catalytic and/or enzyme inhibitors in a saccharide-containing composition. In such a process, calcium oxide (i.e., lime) is added to a crude saccharide-containing composition, thereby increasing the pH, and elevated temperatures and forceful mixing generally are employed. Acid typically is added to the composition to neutralize or acidify it, and solid by-products must be filtered out of the mixture. While an overliming method typically serves to reduce the amount of some by-products in the composition, the process will typically not remove organic acids (e.g. formic acid, levulinic acid, acetic acid, glycolic acid), which may inhibit fermentation and catalysis. Furthermore, overliming can be undesirable due to the large scale requirements, high cost, potential sugar degradation, and potentially large amount of waste (gypsum or other neutralization salt) generated.

A further by-product from the hydrolysis process to monosaccharides involves a set of equilibrium reactions that form reversion sugars (from condensation of two, occasionally three, monosaccharide units). Most microorganisms used in the fermentation of saccharides to ethanol and/or butanol cannot process many of the reversion sugars. As such, the reversion sugars are considered a waste material. This side-reaction to form reversion sugars becomes more prevalent at higher hydrolysis concentrations, and has historically capped the operating concentrations in the acid hydrolysis reaction, which, in turn, has adversely affected the economics of the process.

Thus, there continues to be a need for providing an improved method of hydrolyzing an oligosaccharide stream to monosaccharides, wherein the method results in reduced operating costs, reduced by-products (especially organic acids), and/or improved quality of the monosaccharides produced from the process.

It will be appreciated that this background description has been created by the inventors to aid the reader and is not to be taken as an indication that any of the indicated problems were themselves appreciated in the art. While the described principles can, in some aspects and embodiments, alleviate the problems inherent in other systems, it will be appreciated that the scope of the protected innovation is defined by the attached claims and not by the ability of any disclosed feature to solve any specific problem noted herein.

BRIEF SUMMARY OF THE INVENTION

Described herein is a method comprising
(a) providing a hydrolysis composition of at least 20 wt % of sugar equivalents, wherein the hydrolysis composition comprises a first oligosaccharide, water, optionally a soluble aromatic compound, and optionally organic and/or inorganic impurities,
(b) contacting the hydrolysis composition with a catalyst in a first reactor to hydrolyze at least a portion of the first oligosaccharide to form a first product composition comprising a first monosaccharide and a second oligosaccharide,
(c) separating the first monosaccharide from the first product composition to form a second product composition comprising the second oligosaccharide, wherein at least a portion of the second oligosaccharide is a reversion sugar, and
(d) converting via a further hydrolysis step at least a portion of the second oligosaccharide to form a third product composition comprising a second monosaccharide.

DETAILED DESCRIPTION OF THE INVENTION

Figure 1:
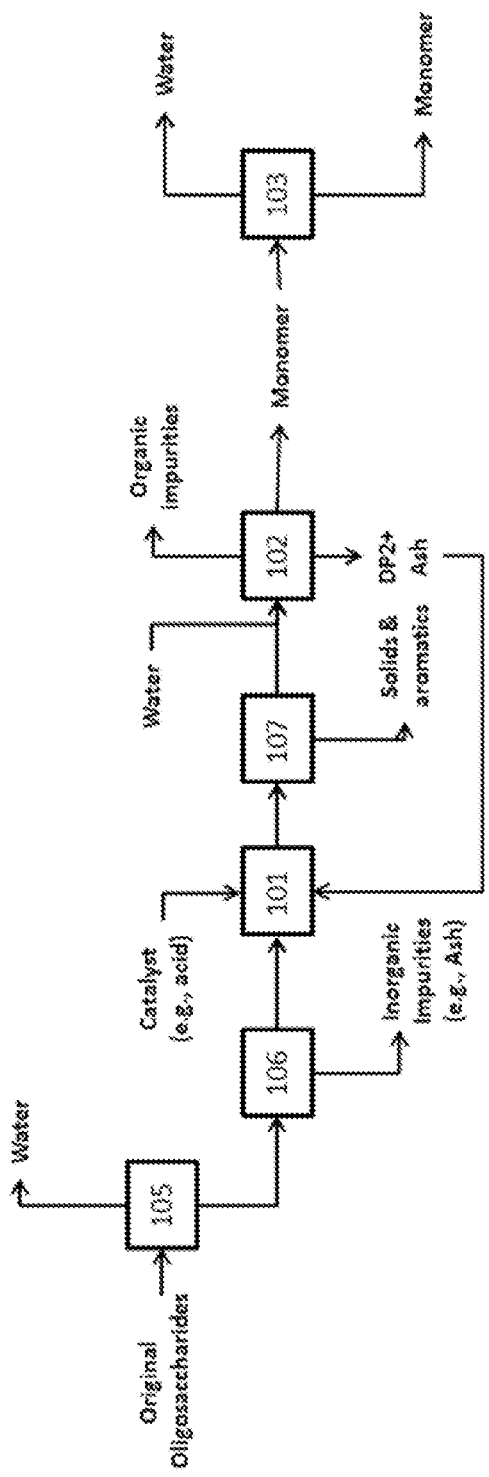
FIG. 1 is a block flow diagram of an exemplary hydrolysis process showing an option for routing the at least partially hydrolyzed oligosaccharide (e.g., second oligosaccharide) back to the first hydrolysis reactor (101).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted.

As used herein the term "about" typically refers to ±1% of a value, ±5% of a value, or ±10% of a value.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading or in any portion of the disclosure may be combined with embodiments illustrated under the same heading or portion of the disclosure, or under any other heading or other portion of the disclosure.

Any combination of the elements described herein in all possible variations thereof is encompassed by the invention unless otherwise indicated herein or otherwise clearly contradicted by context.

Unless otherwise expressly stated, it is in no way intended that any method or aspect set forth herein be construed as requiring that its steps be performed in a specific order. Accordingly, where a method claim does not specifically state in the claims or description that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, or the number or type of embodiments described in the specification.

The use of numerical values in the various quantitative values specified in this application, unless expressly indicated otherwise, are additionally stated, in the alternative, as approximations as though the minimum and maximum values within the stated ranges were both preceded by the word "about." In this manner, slight variations from a stated value may be used to achieve substantially the same results as the stated value. Also, the disclosure of ranges is intended as a continuous range including every value between the minimum and maximum values recited as well as any ranges that may be formed by such values. For example, a disclosure that a component may be present in an amount of from 2% to 10% would include, among others from 2% to 9%, 2% to 8%, 3% to 10%, 3% to 9%, 4% to 5%, etc. Also disclosed herein are any and all ratios (and ranges of any such ratios) that may be formed by dividing a recited numeric value into any other recited numeric value. Accordingly, the skilled person will appreciate that many such ratios, ranges, and ranges of ratios may be unambiguously derived from the numerical values presented herein and in all instances such ratios, ranges, and ranges of ratios represent various embodiments of the present invention.

When disclosing numerical values herein, for example, 1, 2, 3, 4, 5, 6, 7, 8, 9, 10, the following sentence may follow such numerical values: "Each of the foregoing numbers can be preceded by the term 'about,' 'at least about,' or 'less than about,' and any of the foregoing numbers can be used singly to describe an open-ended range or in combination to describe a closed-ended range." This sentence means that each of the aforementioned numbers can be used alone (e.g., 4), can be prefaced with the word "about" (e.g., about 8), prefaced with the phrase "at least about" (e.g., at least about 2), prefaced with the phrase "less than about" (e.g., less than about 7), or used in any combination with or without any of the prefatory words or phrases to define a range (e.g., 2 to 9, about 1 to 4, 8 to about 9, about 1 to about 10, and so on). Moreover, when a range is described as "about X or less" (where X is a number), this phrase is the same as a range that is a combination of "about X" and "less than about X" in the alternative. For example, "about 10 or less" is the same as "about 10, or less than about 10." Such interchangeable range descriptions are contemplated herein. Other range formats may be disclosed herein, but the difference in formats should not be construed to imply that there is a difference in substance.

As used herein, the term "hydrolysis composition" means a composition that undergoes a hydrolysis reaction.

As used herein, the term "degree of polymerization" (DP) is defined as the number of monomeric units in a macromolecule or polymer or oligomer. For example and without limitation, the number-average degree of polymerization is given by:

$$DP_n = X_n = \frac{M_n}{M_0}$$

where $M_n$ is the number-average molecular weight and $M_0$ is the molecular weight of the monomer unit. For cellulose, the monomer unit is the anhydroglucose unit (glucose minus the equivalent of one water molecule, 162 g/mol).

As used herein, "oligosaccharide" refers to linear or branched carbohydrate molecules of the same or different monosaccharide units joined together by glycosidic bonds having the general formula of $C_x(H_2O)_y$. Oligosaccharides may be thought of as shorter chain polysaccharides, i.e., polysaccharides simply having less monomeric residues in the polymeric chain. When an oligosaccharide contains $C_6$ monosaccharide residues, the general formula may be represented as $(C_6H_{10}O_5)_n$, where n is about 2 to about 15 (i.e., the number of hexose monomers in the oligosaccharide). As used herein, an oligomer (e.g., cello-oligosaccharide) has a DP in the range of 2 to about 15 (i.e., DP2 to DP15), whereas a polymer (e.g., cellulose) has a DP of at least about 16.

As used herein, "monosaccharide" refers to any of the class of sugars that cannot be hydrolyzed to give a simpler sugar. Monosaccharides typically are $C_5$ (e.g., xylose) and $C_6$ sugars (e.g., glucose), but may also include monosaccharides having other numbers of carbons, such as $C_3$, $C_4$, $C_7$, $C_8$, and so on. Expressed another way, monosaccharides are the simplest building blocks of oligosaccharides and polysaccharides. Monosaccharides of cellulose are predominantly $C_6$ saccharides (e.g., glucose).

As used herein the term "sugar equivalents" refers to all saccharides (polysaccharides, oligosaccharides, and monosaccharides), including in both dissolved (monosaccharides and lower DP oligosaccharides) and solid forms (higher DP oligosaccharides and polysaccharides including, if present, cellulose, hemicellulose and starch), expressed as the total mass of monosaccharides that would result if all such saccharides are hydrolyzed to monosaccharides.

As used herein the term "wt % of sugar equivalents" refers to the weight of sugar equivalents present in a solution or composition, expressed as a percentage of the total weight of the solution or composition.

As used herein the term "wt % of total non-aqueous components" refers to the total weight of all components, other than water, in a solution or composition, expressed as a percentage of the total weight of the solution or composition.

The economics of hydrolysis processes described herein improve by increasing the saccharide concentration in an oligosaccharide-containing composition, since lower capital cost derives from requiring smaller reaction vessels and lower operating cost derives from requiring less acid to achieve the target pH. In addition, using less catalyst, which typically is acidic, means less base is required to neutralize the reaction in a smaller reactor. This, in turn, means less solid by-product, such as gypsum ($CaSO_4.2H_2O$), is formed, thereby reducing the solids disposal cost and capital in the form of a filter. However, there is a constraint on the concentration of the oligosaccharide-containing composition in the form of a reversion equilibrium. In particular, as the monomer concentration increases, reversion sugars (e.g., dimer) are formed in an amount approximately proportional to the monomer concentration squared. In the context of fermentation of saccharides to biofuels, the reversion sugar is regarded as a yield loss (since most microorganisms cannot process some or all of the reversion sugars) and negatively impacts the economics of the hydrolysis. For most applications, this limits the concentration of the hydrolysis composition to an oligosaccharide concentration of about 150 g/l (i.e., about 15 wt %) of sugar equivalents to minimize yield loss to reversion sugars. The methods herein seek to relieve this constraint by separating oligomer (i.e., degree of polymerization of 2 or more) from monomer to improve the overall yield and/or quality of the production of monosaccharide, and allow a much higher oligosaccharide concentration in the hydrolysis composition, typically about 40-60 wt % or more of sugar equivalents. Further, if the oligomers can be recovered and recycled, the extent of hydrolysis for a single pass through the reactor can be reduced while maintaining the overall process yield. This reduced extent of reaction reduces the breakdown of monomers to impurities (such as HMF, furfural and organic acids), and thus provides a resultant sugar stream with lower levels of fermentation inhibitors.

Accordingly, provided is a method comprising:

(a) providing a hydrolysis composition of at least 20 wt % of sugar equivalents, wherein the hydrolysis composition comprises a first oligosaccharide, water, optionally a soluble aromatic compound (e.g., lignin and/or humins), and optionally organic and/or inorganic impurities, (b) contacting the hydrolysis composition with a catalyst in a first reactor to hydrolyze at least a portion of the first oligosaccharide to form a first product composition comprising a first monosaccharide and a second oligosaccharide, (c) separating the first monosaccharide from the first product composition to form a second product composition comprising the second oligosaccharide, wherein at least a portion of the second oligosaccharide is a reversion sugar, and (d) converting via a further hydrolysis step at least a portion of the second oligosaccharide to form a third product composition comprising a second monosaccharide.

The hydrolysis composition typically comprises a first oligosaccharide. The first oligosaccharide typically is a C5 or C6 oligosaccharide, and in certain embodiments may include mixtures thereof. A C5 oligosaccharide includes an oligosaccharide comprising a five-carbon sugar, such as those described herein, including xylose (e.g., xylose monomeric units). A C6 oligosaccharide includes an oligosaccharide comprising a six-carbon sugar, such as those described herein, including glucose (e.g., glucose monomeric units). Hydrolysis (or partial hydrolysis) of the first oligosaccharide produces the first product composition, comprising the second oligosaccharides and first monosaccharide. Depending on the chemical structure of the first oligosaccharide, the first monosaccharide is a C5 monosaccharide (e.g., arabinose, lyxose, ribose, xylose, ribulose, and xylulose), a C6 monosaccharide (e.g., allose, altrose, glucose, mannose, rhamnose, gulose, idose, galactose, talose, psicose, fructose, sorbose, and tagatose), or a mixture thereof. In certain embodiments, the first monosaccharide is a C6 monosaccharide, such as glucose. In some embodiments, at least a portion of the first oligosaccharide is a recycled second oligosaccharide as described elsewhere herein.

In the methods described herein, the monosaccharide product typically is separated out from the first product composition resulting in a second product composition. The second product composition comprises the second oligosaccharide (typically shorter chain oligosaccharides on average than the first oligosaccharide), in which at least a portion of the second oligosaccharide is a reversion sugar. The second oligosaccharide may additionally or alternatively comprise first oligosaccharide that has been at least partially hydrolyzed. The second oligosaccharide may comprise the same monomeric units as the first oligosaccharide. As used herein, a "reversion sugar" is a sugar that is formed when a monosaccharide condenses with another monosaccharide (occasionally, disaccharide) in the presence of a catalyst (e.g., acid) to form an oligosaccharide, such as (predominantly) a disaccharide or (rarely) a trisaccharide. As a result, in many cases the reversion sugar has a bonding linkage that is not present in the original biomass. For example, gentiobiose is a reversion sugar composed of two glucose units bonded together with a β-(1,6) linkage. This bonding linkage is not present in native biomass, which is composed of cellulose having glucose units bonded in a β(1,4) arrangement. However, reversion sugars may also be sugars having linkages that are present in the original biomass, such as cellobiose and xylobiose. Examples of reversion sugars include, for example, xylobiose, (both α- and β-forms of (1,1), (1,2), (1,3), and (1,4)-linked xylobiose), O-α-D-xylopyranosyl-α-D-xylopyranoside, 3-O-α-D-xylopyranosyl-D-xylose, 2-O-α-D-xylopyranosyl-D-xylose, 4-O-α-D-xylopyranosyl-D-xylose, maltose, isomaltose, cellobiose, gentiobiose, 1,6-anhydro-β-D-glucofuranose, kojibiose, sophorose, nigerose, laminarabiose, and any combination thereof. At least a portion of the reversion sugar will convert back to the monomer (monosaccharide) with the further hydrolysis step described elsewhere herein (especially if that step has a lower glucose equivalent concentration).

In some embodiments, one or more reversion sugars are present in a hydrolyzing step (e.g., the contacting step or further hydrolysis step) or in a product composition (e.g., first or second product composition) in an amount of 0.2, 0.4, 0.6, 0.8, 1, 1.2, 1.4, 1.6, 1.8, 2, 2.2, 2.4, 2.6, 2.8, 3, 3.2, 3.4, 3.6, 3.8, 4, 4.2, 4.4, 4.6, 4.8, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, or 30 g/kg, based on the total weight of the composition (e.g., the composition employed in the step or the first or second product composition). Each of the foregoing numbers can be preceded by the word "about," "at least about," or "less than about," and any of the foregoing numbers can be used singly to describe an open-ended range or in combination to describe a close-ended range. In some embodiments, a hydrolyzing step (e.g., the contacting step or further hydrolysis step) is performed at conditions sufficient to form one or more reversion sugars in any of the amounts specified herein. In some embodiments, these amounts of reversion sugars can refer to any of the individual reversion sugars disclosed herein, or any combination of the individual reversion sugars. For example, in some embodiments, the reversion sugar is gentiobiose, and the amount of gentiobiose can be present in a product composition or step in any of the amounts disclosed herein. In some embodiments, the reversion sugars are or comprise gentiobiose and xylobiose, and the amount of this combination (gentiobiose and xylobiose) can be present in a product composition or step in any of the amounts disclosed herein. Any other pairing of reversion sugar(s) and amounts can be made.

In the figures described herein, features having the same numbers in different figures serve the same or similar functions.

FIG. 1 depicts a block flow diagram that illustrates an embodiment of the methods disclosed herein. In particular, the hydrolysis composition, comprising a first oligosaccharide and typically having an oligosaccharide content of about 40-60 wt % of sugar equivalents, is provided in a first reactor 101. The first oligosaccharide may be derived, for example, from an original oligosaccharide composition produced by sub-, near-, or supercritical hydrolysis of a biomass feedstock as described elsewhere herein. Optionally, the original oligosaccharide composition may be concentrated in apparatus 105 (e.g., an evaporator) and inorganic impurities may be removed using separation apparatus 106 (e.g., an ion exchange resin). In reactor 101, the hydrolysis composition is at least partially hydrolyzed to form the first product composition, which may be routed to separation apparatus 102. Soluble aromatic compounds (e.g., lignin and/or humins), if present, typically precipitate under acid conditions, especially at a pH of less than about 2. Accordingly, as an alternative, optionally, a partial separation may be performed in separation apparatus 107 where the previously soluble aromatic compounds, but now precipitated, may be removed (e.g., by use of a solid-liquid separation apparatus, such as a filter) prior to routing the first product composition to separation apparatus 102. In separation apparatus 102, the first monosaccharide product can be separated and moved to vessel 103. Excess water can be removed (e.g., evaporated) in vessel 103, if desired, and the resulting first monosaccharide can be stored or further processed, such as undergo a fermentation process.

Figure 2:
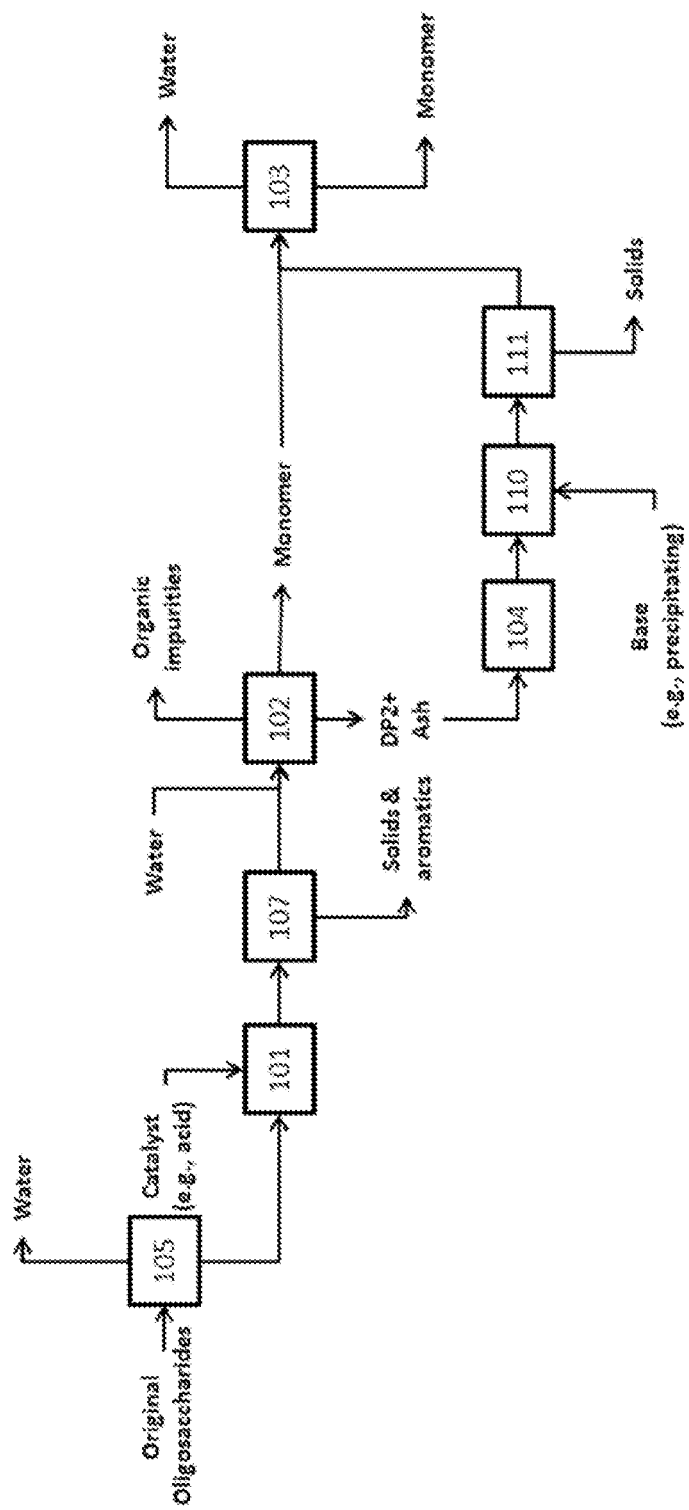
FIG. 2 is a block flow diagram of an exemplary hydrolysis process showing an option for routing the at least partially hydrolyzed oligosaccharide (e.g., second oligosaccharide) to a further hydrolysis step in a second reactor (104).
Figure 3:
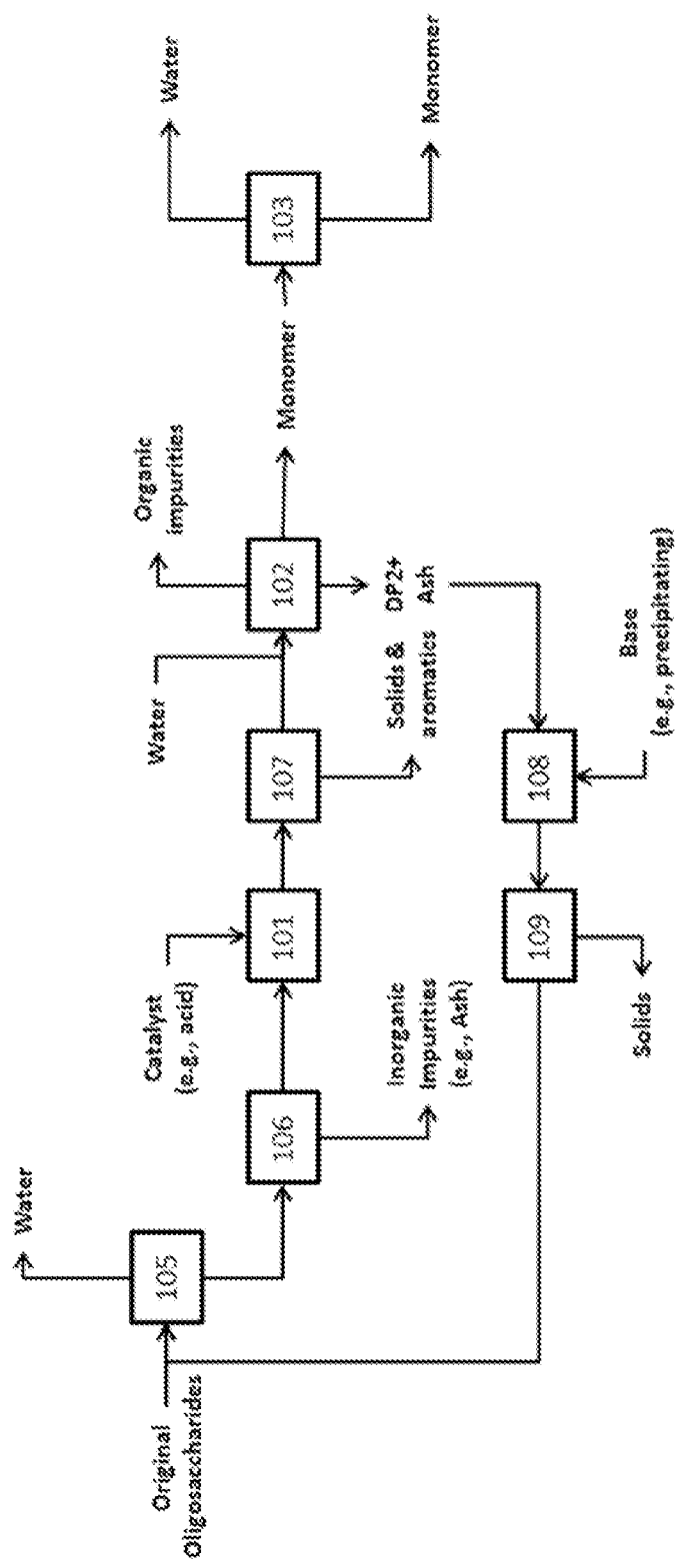
FIG. 3 is a block flow diagram of an exemplary hydrolysis process showing an option for routing the at least partially hydrolyzed oligosaccharide (e.g., second oligosaccharide) to a concentrating vessel (105) before returning to the first hydrolysis reactor (101). A neutralizing step (followed by separation of precipitate) is shown prior to entry in the concentrating vessel (105).

After separating the first monosaccharide, the second product composition can optionally be further processed via a further hydrolysis step as discussed further herein (e.g., as shown in FIGS. 1, 2 and 3). At this stage of the process, the concentration of the second product composition typically is much lower than the concentration of the first product composition. For example, the solids content of the second product composition (on a sugar equivalents basis) can be one tenth, one fifth, one quarter, one third, or one half of the solids content of the first product composition (on a sugar equivalents basis), or any of the other amounts described elsewhere herein for the second product composition.

The further hydrolysis step may be performed, for example, according to one or more of the embodiments depicted in FIGS. 1, 2 and 3, or as described elsewhere herein.

In one embodiment (as depicted in FIG. 1), the further hydrolysis step (i.e., step (d)) comprises step (e) recycling at least a portion of the second oligosaccharide back to the first reactor 101 (optionally, via concentrating vessel 105, and separating vessel 106, although in a continuous process the highly acidic composition may degrade the apparatus), and a step (f) of repeating steps (b)-(d) of the method using the portion of the second oligosaccharide as at least a portion of the first oligosaccharide. If desired, a portion of the previous hydrolysis composition (~60 wt % of sugar equivalents) can be combined with the second product composition to ensure that the solids content of the new hydrolysis composition is at least 20 wt % of sugar equivalents, as described herein.

In another embodiment (as depicted in FIG. 2), the further hydrolysis step (i.e., step (d)) can alternatively or additionally occur in a second reactor 104. In an embodiment, the second monosaccharide has the same structure as the first monosaccharide (e.g., both the first and second monosaccharides are glucose). The second reactor can be different from the first reactor, such as reaction vessel 104 in FIG. 2. Typically, with this setup, the catalyst for the further hydrolysis reaction in 104 is an acid, as described herein, resulting in a low pH for the second oligosaccharide (and also the third product composition). In this aspect, the method can further comprise adjusting the pH of the third product composition by addition of a base (e.g., a precipitating base), which may occur in the same vessel (reactor 104) or a separate vessel, such as in vessel 110 in FIG. 2. A pH adjustment (to ~pH=3) is sometimes preferable because the acid hydrolysis reaction is typically performed at a pH of ~1; concentrating such a low pH solution produces a very corrosive liquid which would likely damage most economically feasible materials of construction. When the second monosaccharide is produced, the second monosaccharide can be collected separately or can be collected and then combined with the first monosaccharide. In a preferred embodiment, the second monosaccharide is combined with the first monosaccharide after removal of any precipitated solids (e.g. gypsum) in a suitable device 111, such as a filter.

In yet a further embodiment (as depicted in FIG. 3), the method can further comprise, prior to the further hydrolysis step (d), a step (e) of increasing the pH of the second product composition in vessel 108 to form a pH-adjusted second product composition. Typically, the catalyst for the hydrolysis reaction in reactor 101 is an acid, as described herein. Again, pH-adjustment (to ~pH=3) (vessel 108) is sometimes preferable because the acid hydrolysis reaction in reactor 101 is typically performed at a pH of ~1 and the second product composition (comprising second oligosaccharide and unreacted acid) is also strongly acidic; concentrating such a solution produces a very corrosive liquid which would likely damage most economically feasible materials of construction. After pH adjustment, a device 109, for example a filter, may be used to remove any precipitate (e.g., gypsum). The method may further comprise a step (f) of concentrating the pH-adjusted second product composition in vessel 105 (e.g., an evaporator) to at least 20 wt % of sugar equivalents to form a concentrated pH-adjusted second product composition, and recycling the concentrated pH-adjusted second product composition to a second reactor. In some embodiments, the second reactor is different from the first reactor 101, but in other embodiments, the second reactor is the same as the first reactor 101. Preferably, the second reactor is the same as the first reactor 101, as shown in FIG. 3.

The pH of the second product composition or the third product composition in any embodiment herein can be adjusted, if desired, with a suitable base to a pH of at least 2.5. The pH may be adjusted to 2.5, 3, 3.5, 4, 4.5, 5, 5.5, 6, 6.5, 7, 7.5, 8, 8.5, 9, 9.5, 10, 10.5, 11, 11.5, or 12. Any suitable base as described elsewhere herein may be employed. Each of the foregoing numbers can be preceded by the word "about," "at least about," or "less than about," and any of the foregoing numbers can be used singly to describe an open-ended range or in combination to describe a close-ended range. For example, and without limitation, if the second product composition has been subjected to a further hydrolysis step (e.g., in vessel 104) and then a base is added, the base typically is added in an amount to adjust the pH to at least 2.5, such as a pH of about 3-7, or any other pH described herein. Alternatively, if the base is added to the second product composition prior to a further hydrolysis step, the base is added in an amount, for example, to adjust the pH to about 3-5, or any other pH described herein. In certain embodiments, the base is a precipitating base. For example, if the hydrolysis is performed using sulfuric acid, then the precipitating base typically may comprise CaO, $CaCO_3$, MgO, $Ca(OH)_2$, or $NH_4OH$, or any combination thereof. However, a precipitating base need not be used, and in some embodiments a precipitating base is not used. Other suitable bases include alkali metal hydroxides and alkaline earth metal hydroxides (e.g., lithium hydroxide, sodium hydroxide, potassium hydroxide, rubidium hydroxide, cesium hydroxide, magnesium hydroxide, strontium hydroxide, barium hydroxide, and combinations thereof), sodium carbonate, and/or potassium carbonate, or any combination thereof.

The method (as depicted in FIG. 2 or FIG. 3) optionally further comprises removing any solid by-product that is formed upon addition of the precipitating base via, for example, separation apparatus 111 (FIG. 2) or 109 (FIG. 3). For example, the addition of lime (CaO) will form the solid by-product $CaSO_4.2H_2O$, i.e., gypsum, when sulfuric acid is used as the hydrolysis catalyst. Although by-products such as furfural and hydroxymethylfurfural (HMF) should be soluble in water, some quantity may be adsorbed onto the precipitate and possible condensation/polymerization products of furfural and HMF may also precipitate. Any solid by-products can be removed by any suitable method, such as filtration, centrifugation, decanting, or any combination thereof.

Figure 4:
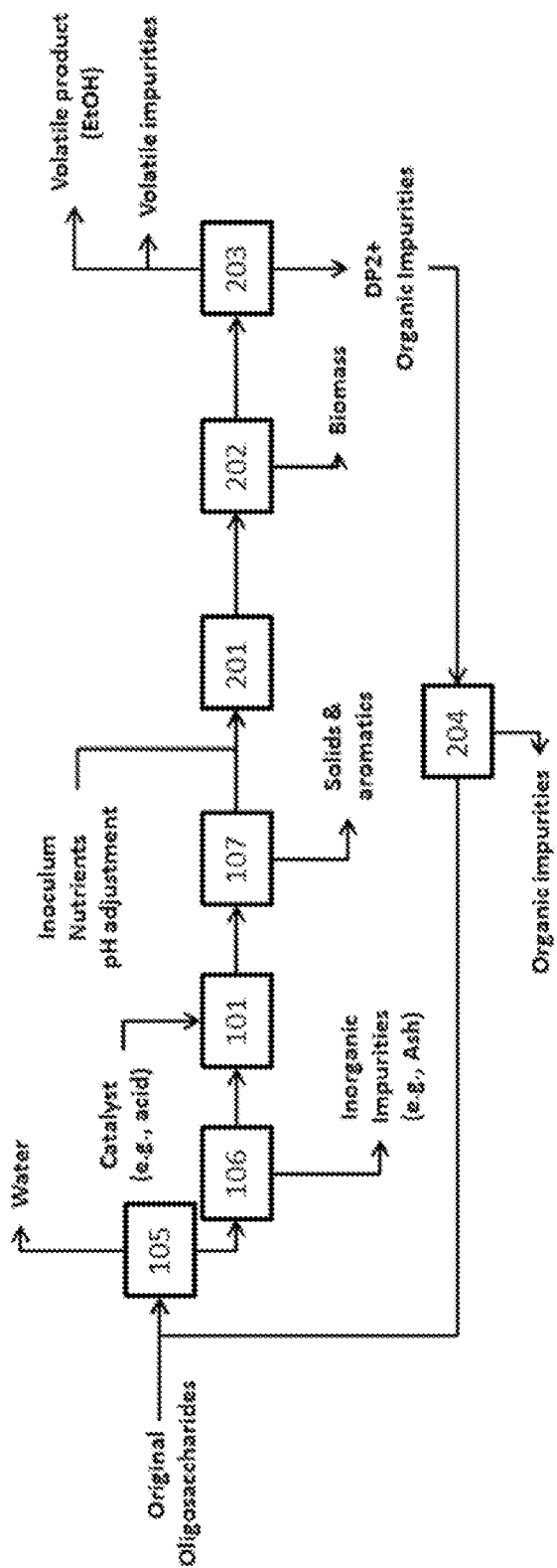
FIG. 4 is a block flow diagram of an exemplary hydrolysis process showing an option for separating the monosaccharide product from the hydrolysis reaction product mixture using a fermentation process.

In yet another embodiment (and as depicted in FIG. 4), the separation of the monosaccharide from the oligosaccharides can be performed by a fermentation process (performed in a fermentation vessel 201 in FIG. 4). The first product composition from the hydrolysis reaction in 101, optionally after removal of solids and aromatic compounds (in separation apparatus 107) and optionally before entering fermentation vessel 201, is combined with the appropriate inoculum, nutrients and pH adjustment required for fermentation of monosaccharides. During the fermentation process, monosaccharides are consumed to, or nearly or partially to, exhaustion and fermentation products, such as ethanol, are produced. Cell recovery can occur (for example, by filtration, decantation, or centrifugation, or any combination thereof) in separation apparatus 202 before (or after) separation of volatile compounds (including fermentation product ethanol) occurs in vessel 203 (for example, a distillation column). Most microorganisms cannot process some or all of the oligosaccharides. The oligosaccharides (DP2 and higher) and organic impurities can be routed to another separation step (separation apparatus 204, such as, for example, an ion exchange column) to remove organic impurities. The oligosaccharides (DP 2 and higher) may then proceed to further hydrolysis (as described elsewhere herein and as depicted, for example, in FIGS. 1, 2 and 3) in order to convert the oligosaccharides (including reversion sugars) to monosaccharides. Variations of this embodiment are also contemplated. For example, the separation of organic impurities, shown at separation apparatus 204 in FIG. 4, may alternatively be performed before the fermentation process (shown as fermentation vessel 201 in FIG. 4). Furthermore, either separately, or in addition to this alternative, one could perform an overliming step at any point after the hydrolysis reaction in the hydrolysis reactor 101, and before the fermentation process in fermentation vessel 201.

The amount of sugar equivalents in the hydrolysis composition is at least 20 wt % of the total weight of the composition. The wt % of sugar equivalents in the hydrolysis composition can be 15, 20, 25, 30, 35, 40, 45, 50, 55, 60, 65, 70, 75, 80, 85, 90, or 95. Each of the foregoing numbers can be preceded by the word "about," "at least about," or "less than about," and any of the foregoing numbers can be used singly to describe an open-ended range or in combination to describe a close-ended range. For example, and without limitation, the wt % of sugar equivalents can be about 25-90 wt %, about 30-90 wt %, about 30-85 wt %, about 40-80 wt %, about 50-70 wt %, or about 55-65 wt %. In a particular example, the wt % of sugar equivalents is about 60 wt %. The wt % of sugar equivalents in the hydrolysis composition is independent of, i.e., can be the same or different from, the wt % of sugar equivalents in the pH-adjusted second product composition.

Following the methods disclosed herein, the upper end of the solids content of the saccharide-containing compositions is not constrained by the sugars content per se, but typically will depend on the viscosity of the particular composition, which in turn is dependent on all species present (e.g., first oligosaccharide, optionally a soluble aromatic compound, optionally organic and inorganic impurities, and any other species present), herein collectively referred to as "non-aqueous components." Depending on the source of the first oligosaccharide, the content of non-aqueous components can be as high as 95 wt %. In general, however, the content of non-aqueous components in the saccharide-containing compositions (including the hydrolysis composition) can be 15, 20, 25, 30, 35, 40, 45, 50, 55, 60, 65, 70, 75, 80, 85, 90, or 95 wt % of total non-aqueous components. Each of the foregoing numbers can be preceded by the word "about," "at least about," or "less than about," and any of the foregoing numbers can be used singly to describe an open-ended range or in combination to describe a close-ended range. For example, and without limitation, the non-aqueous components can be present in an amount of about 25-90 wt %, about 30-90 wt %, about 30-85 wt %, about 40-80 wt %, about 50-75 wt %, or about 60-75 wt %. In a particular example, the amount of non-aqueous components is about 70 wt %.

The amount of non-aqueous components of a composition can be adjusted by any suitable method, including, for example, evaporation of water using any suitable method or apparatus, such as an evaporator or steam stripper. In reference to the figures, such apparatuses are represented by vessel 105.

The original oligosaccharide composition can be initially provided with a content of less than 20 wt % of sugar equivalents (e.g., 18 wt % or less, 15 wt % or less, 12 wt % or less, 10 wt % or less, 8 wt % or less, 5 wt % or less, 4 w % or less, 3 wt % or less, 2 wt % or less, or 1 wt % or less). In such an instance, water can be removed (e.g., evaporated in vessel 105) in order to concentrate the composition and provide a content of at least 20 wt % of sugar equivalents for the hydrolysis composition. In a particular example, the original oligosaccharide composition is initially provided with a content from 5-10 wt % of sugar equivalents, and the composition is concentrated (e.g., in vessel 105) to a content of about 40-60 wt % of sugar equivalents for the hydrolysis composition.

The second product composition can have for example, about 1, 2, 5, 10, 15, 20, 25, 30, 35, or 40 wt % of sugar equivalents. Each of the foregoing numbers can be preceded by the word "about," "at least about," or "less than about," and any of the foregoing numbers can be used singly to describe an open-ended range or in combination to describe a close-ended range. For example and without limitation, the solids content of the second product composition can be at least about 1, about 5 to about 30, about 10 to about 25, or less than about 30 wt % of sugar equivalents.

A hydrolysis step (e.g., the contacting step or further hydrolysis step) can be carried out at any suitable temperature (° C.), such as 30, 40, 50, 60, 70, 80, 90, 100, 110, 120, 130, 140, 150, 160, 170, 180, 190, 200, 210, 220, 230, 240, 250, or 260. Each of the foregoing numbers can be preceded by the word "about," "at least about," or "less than about," and any of the foregoing numbers can be used singly to describe an open-ended range or in combination to describe a close-ended range. For example, and without limitation, the hydrolysis step can be carried out at a temperature of at least about 90, or about 90-260° C. or about 100-225° C., or about 100-140° C., or less than about 250° C.

The catalyst is any suitable compound that can facilitate hydrolysis of an oligosaccharide into shorter chain length oligosaccharides (i.e., degree of polymerization of 2 or more) and/or monosaccharides. Suitable catalysts include, for example, strong acids, strong bases, and enzymes. Suitable strong acids include a mineral acid (e.g., sulfuric acid, hydrochloric acid, hydrofluoric acid, hydrobromic acid, hydroiodic acid, nitric acid, phosphoric acid, chloric acid, perchloric acid, boric acid, sulfurous acid, nitrous acid, phosphorous acid, and any combination thereof), strong organic acids (e.g., p-toluenesulfonic acid, methanesulfonic acid, perfluorosulfonic acids (such as trifluoromethane sulfonic acid), trifluoroacetic acid, oxalic acid, maleic acid, fumaric acid, and any combination thereof), or any combination thereof. More than one kind of acid can be used. In some embodiments, the mineral acid is hydrochloric acid or sulfuric acid (e.g., 70% sulfuric acid). A strong base includes alkali metal hydroxides and alkaline earth metal hydroxides (e.g., lithium hydroxide, sodium hydroxide, potassium hydroxide, rubidium hydroxide, cesium hydroxide, magnesium hydroxide, calcium hydroxide, strontium hydroxide, barium hydroxide, and combinations thereof), ammonium hydroxide, sodium carbonate, potassium carbonate, and/or calcium carbonate. Suitable enzymes include cellulases (e.g., CelA, CelB, and β-glycosidase), xylanases, laccases, and peroxidases (e.g., *Trametes versicolor*). However, strong acids are more commonly used for the hydrolysis reaction because enzymes are more expensive, and strong bases produce a greater proportion of fructose, which breaks down to side-products more easily.

When run at a higher concentration compared to lower concentration, less catalyst per mass of sugar equivalents is required to catalyze the hydrolysis reaction, which represents a cost savings and potentially an easier reaction setup (e.g., smaller reactors). In a specific example, less acid as the catalyst means less base is subsequently required to neutralize the acid, which results in a lower amount of by-products (e.g., solid by-products that precipitate), again leading to a reduction in cost and capital. Additionally, in an embodiment, the acid can be recovered and/or recycled in the system to further reduce cost.

The catalyst is used in any suitable amount (wt % of active catalyst component, e.g., $H_2SO_4$, based on total weight of composition), such as 0.01, 0.02, 0.03, 0.04, 0.05, 0.06, 0.07, 0.08, 0.09, 0.1, 0.15, 0.2, 0.3, 0.4, 0.5, 0.6, 0.7, 0.8, 0.9, 1, 1.5, 2, 2.5, 3, 3.5, 4, 4.5, or 5. Each of the foregoing numbers can be preceded by the word "about," "at least about," or "less than about," and any of the foregoing numbers can be used singly to describe an open-ended range or in combination to describe a close-ended range. For example, and without limitation, the amount of catalyst (e.g., mineral acid) can be at least about 0.05 wt %, such as about 0.05 to about 2, about 0.1 to about 1, or about 0.5 wt %.

The amount of catalyst employed can also be expressed in terms of pH. In this regard, the pH employed to hydrolyze the first oligosaccharide into the second oligosaccharide can be −2, −1.5, −1, −0.5, 0, 0.2, 0.5, 1, 1.5, 2, 2.5, 3, 3.5, 4, 4.5, 5, 5.5, or 6. Each of the foregoing numbers can be preceded by the word "about," "at least about," or "less than about," and any of the foregoing numbers can be used singly to describe an open-ended range or in combination to describe a close-ended range. For example, and without limitation, the pH can be at least 0.2, such as about 0.5 to about 2, for example about 1.

In the hydrolysis step (i.e., step (b)), the first oligosaccharide is at least partially hydrolyzed to form a first product composition comprising a first monosaccharide and a second oligosaccharide. At least partially hydrolyzing the first oligosaccharide means that not only monomer is formed but small oligomers are also formed, such as dimers and trimers. Thus, a partial hydrolysis in which monomer is then separated from the rest of the composition reduces the amount of time the monomer has available to break down to smaller molecules, which leads to a reduction in the amount of by-products formed in the reaction. A reduction or even elimination of monomer break down products (e.g., organic acid and/or aldehyde compounds) decreases or even possibly avoids the need for overliming.

As used herein, the term "at least partially hydrolyzed" or "partially hydrolyzed" or "hydrolyze at least a portion of" means that at least 10, 12, 15, 18, 20, 25, 30, 35, 40, 45, 50, 55, 60, 65, 70, 75, 80, 85, 90, 95, or 99 wt % of the first oligosaccharide is hydrolyzed to form the first monosaccharide. Each of the foregoing numbers can be preceded by the word "about," "at least about," or "less than about," and any of the foregoing numbers can be used singly to describe an open-ended range or in combination to describe a close-ended range. For example, and without limitation, the amount of first oligosaccharide hydrolyzed to monosaccharide can be at least 20 wt %, or from 10 to 90 wt %, or from 40 to 75 wt %. The percentage of the partial hydrolysis can be controlled by the reaction conditions, such as the hydrolysis temperature, reaction time, catalyst amount, pH, and/or amount of solids in the composition.

In some embodiments, no more than 5, 10, 15, 20, 25, 30, 35, 40, 45, 50, 55, 60, 65, 70, 75, 80, 85, 90, or 95 wt % of the first oligosaccharide (or second oligosaccharide) is hydrolyzed in a hydrolysis step (e.g., the contacting step or further hydrolysis step) to form the first monosaccharide (or second monosaccharide). Each of the foregoing numbers can be preceded by the word "about," or "less than about," and any of the foregoing numbers can be used singly to describe an open-ended range or in combination to describe a close-ended range. For example, and without limitation, the amount of first oligosaccharide hydrolyzed to monosaccharide can be no more than 50 wt %, or no more than 85 wt %, or no more than 95 wt %, or from 40 to 95 wt %, or from 65 to 85 wt %. The percentage of the partial hydrolysis can be controlled by the reaction conditions, such as the hydrolysis temperature, reaction time, catalyst amount, pH, and/or amount of solids in the composition.

The hydrolysis composition comprising the first oligosaccharide can optionally contain at least one soluble aromatic compound. For example, soluble aromatic compounds may include, for example, lignin and humins. A soluble aromatic compound can be present in any or all of the hydrolysis composition, the first product composition, the second product composition, and the third product composition. In an embodiment, the soluble aromatic compound is lignin. If a soluble aromatic compound is present in the hydrolysis composition, the method optionally can further comprise separating at least a portion of the soluble aromatic compound from the composition before or after step (b), for example, in separation apparatus 107. In an embodiment, separation apparatus 107, for example, may be a filtration apparatus, a chromatography apparatus, or both. Under acidic conditions (e.g., a pH of about 0-2) for hydrolyzing the first oligosaccharide to form a first product composition, soluble aromatic compounds typically precipitate (particularly at pH less than about 2), which facilitates their removal from the composition.

Similarly, if one or more inorganic impurities are present in the hydrolysis composition comprising the first oligosaccharide, the method can further comprise removing such inorganic impurities prior to step (b). The inorganic impurities can be, for example, ash, which includes various compounds that contain sodium, potassium, calcium, magnesium, aluminum, phosphorus, silicon, iron, carbonates, silicates, oxides, sulfates, and/or phosphates. The inorganic impurities can be removed using any appropriate method (e.g., in separation apparatus 106), such as an ion exchange resin. A positively charged anion exchange resin or a negatively charged cation exchange resin can be used, as appropriate. In the cases where there is potential for a step of recycling second oligosaccharides to the same reactor (e.g., as in FIGS. 1 and 3), then adding an inorganic removal step (106) can mitigate the buildup of inorganic components in the primary reaction system (101).

After the hydrolysis composition is hydrolyzed in step (b), the first product composition may comprise at least one organic acid and/or an aldehyde compound as a by-product. For example, the organic acid can be, e.g., levulinic acid, glycolic acid, acetic acid, and/or formic acid, and the aldehyde compound can be, e.g., furfural, hydroxymethylfurfural (HMF), syringaldehyde, homosyringaldehyde, coniferaldehyde, benzaldehyde, substituted benzaldehyde, vanillin, homovanillin, 4-hydroxy-3-methoxy-cinnamaldehyde, sinapaldehyde, glyceraldehyde, glycolaldehyde and/or acetaldehyde. In an embodiment, the method further comprises separating an organic acid, an aldehyde compound, or both from the first product composition before step (c) and/or from the second product composition after step (c). The method for removing the organic acid and/or aldehyde can be any suitable method. For example, the organic acid and/or aldehyde compound can be removed using chromatography (e.g., column chromatography, liquid chromatography, simulated moving bed chromatography, ion exchange chromatography), a membrane, electrodialysis, steam stripping, or evaporation.

The first monosaccharide can be separated in step (c) using any suitable method, such as chromatography (e.g., column chromatography, liquid chromatography, simulated moving bed chromatography, ion exchange chromatography), a membrane, fermentation, or any combination thereof. For example, the first monosaccharide can be separated using a fermentation process (for example, as described elsewhere herein, and as depicted in FIG. 4) that includes, for example, contacting the first product composition with at least one microorganism to form at least one fermentation product, such as a biofuel (e.g., a bioalcohol and/or biodiesel), acid (e.g., succinic acid, lactic acid, acrylic acid, levulinic acid, etc.), or other chemicals (e.g., furfural, xylitol). Bioalcohols include ethanol and butanol (e.g., n-butanol, isobutanol, 2-butanol, or tert-butanol) whereas biodiesel includes long chain alkyl (methyl, ethyl, and/or propyl) esters, such as fatty acid methyl esters (FAMEs). Preferably, the at least one fermentation product comprises ethanol, butanol, a farnesene compound, or any combination thereof. More preferably, the at least one fermentation product is ethanol. Suitable microorganisms include, for example, a microbial biocatalyst, enzyme, yeast (e.g., *Saccharomyces cerevisiae*, *Kluyveromyces lactis*, *Kluyveromyces lipoltyica*, *Schizosaccharomyces pombe*, *Pichia stipitis*, *Clostridium acetobutylicum*, or *Debaromyces hansenii*), and/or bacteria (e.g., *Zymomonas mobilis*).

If desired, any unreacted acid (e.g. mineral acid) can be removed from the second product composition using any suitable technique, such as chromatography (e.g., column chromatography, liquid chromatography, simulated moving bed chromatography, ion exchange chromatography), extraction, heat, vacuum, or any combination thereof, if the acid is relatively volatile (e.g., hydrochloric acid).

In an embodiment, the organic acid, aldehyde compound, first monosaccharide, unreacted acid, second oligosaccharide, or any combination thereof (any of which may optionally be present) in the first product composition may be separated using simulated moving bed (SMB) chromatography. SMB chromatography is a continuous separation method used for large scale separations, in which the solid phase consists of two or more columns connected in series to form a single loop. For the SMB separations described herein, five or more columns may be preferable. The mobile phase is characterized by inlets of feed (e.g., the first product composition) and eluent (e.g., water), and outlets of raffinate (e.g., fast moving component) and extracts (e.g., slow moving components). The inlets and outlets constantly rotate to provide a simulated moving bed with a continuous flow of solid components in one direction and a continuous flow of liquid in the opposite direction. Under suitable conditions, various components of the first product composition, such as the second oligosaccharide and inorganic components (e.g. acid); the first monosaccharide; and the organic impurities (e.g. organic acids and aldehydes), can be separated with high purity and yield as three distinct cuts. A single SMB system can be used to separate all of the desired components from the first product composition, or a series of SMB systems can be used where one SMB system is used to separate one to two components at a time. Parallel SMB systems also are contemplated in some embodiments to increase efficiency of the overall process.

In some embodiments, the original oligosaccharide composition used as the source for the hydrolysis composition is a product from the hydrolysis of a feedstock comprising a glucan (e.g., cellulose, starch, or a combination thereof). In particular, the hydrolysis composition itself can be a hydrolysis product of any suitable feedstock that contains a glucan, which is typically a biomass feedstock. As used herein, the term "biomass" means a renewable energy source generally comprising carbon-based biological material derived from living or recently living organisms. Suitable feedstocks include lignocellulosic feedstock, cellulosic feedstock, hemicellulosic feedstock, starch-containing feedstocks, and the like, or any combination thereof. The lignocellulosic feedstock can be from any lignocellulosic biomass, such as plants (e.g., duckweed, annual fibers, etc.), trees (softwood or hardwood, e.g., spruce (Norwegian spruce), elm, oak, aspen, pine, poplar, willow, or eucalyptus), bushes, grass (e.g., miscanthus, switchgrass, rye, reed canary grass, giant reed, or sorghum), dedicated energy crops, municipal waste (e.g., municipal solid waste), and/or a by-product of an agricultural product (e.g., corn, sugarcane, sugar beets, pearl millet, grapes, rice, straw, cotton linters). The biomass can be from a virgin source (e.g., a forest, woodland, or farm) and/or a by-product of a processed source (e.g., off-cuts, bark, and/or sawdust from a paper mill or saw mill, sugarcane bagasse, corn stover, palm oil industry residues, branches, leaves, roots, municipal solid waste, waste paper, waste cotton, and/or hemp). Suitable feedstocks may additionally comprise the constituent parts of any of the aforementioned feedstocks, including, without limitation, C6 saccharides (including cellulose, cellobiose, and C6 oligosaccharides), C5 saccharides (including hemicellulose and C5 oligosaccharides), and mixtures thereof.

In an embodiment, the feedstock comprising a glucan undergoes a supercritical hydrolysis (e.g., employing supercritical fluid comprising, consisting of, or consisting essentially of water, or employing mixed supercritical fluids comprising, consisting of, or consisting essentially of two or more fluid components, such as water and an alcohol (e.g., ethanol, methanol, propanol, butanol, or any combination thereof) and/or carbon dioxide or sulfur dioxide) to form an original oligosaccharide composition comprising the first oligosaccharide. A supercritical fluid is a fluid at a temperature above its critical temperature and at a pressure above its critical pressure. A supercritical fluid exists at or above its "critical point," the point of highest temperature and pressure at which the liquid and vapor (gas) phases can exist in equilibrium with one another. Above critical pressure and critical temperature, the distinction between liquid and gas phases disappears. A supercritical fluid possesses approximately the penetration properties of a gas simultaneously with the solvent properties of a liquid. Accordingly, supercritical fluid extraction has the benefit of high penetrability and good solvation.

Reported critical temperatures and pressures include: for pure water, a critical temperature of about 374.2° C., and a critical pressure of about 22,100 kPa (about 221 bar); for carbon dioxide, a critical temperature of about 31° C. and a critical pressure of about 72.9 atmospheres (about 7386 kPa). Near critical water has a temperature at or above about 300° C. and below the critical temperature of water (374.2° C.), and a pressure high enough to ensure that at least a portion of (e.g., all of) the fluid is in the liquid phase. Sub-critical water has a temperature of less than about 300° C. and a pressure high enough to ensure that at least a portion of (e.g., all of) the fluid is in the liquid phase. Sub-critical water temperature may be greater than about 250° C. and less than about 300° C., and in many instances, sub-critical water has a temperature between about 250° C. and about 280° C.

As used herein, a fluid which is "supercritical" (e.g. supercritical water, supercritical ethanol, supercritical $CO_2$, etc.) indicates a fluid which would be supercritical if present in pure form under a given set of temperature and pressure conditions. For example, "supercritical water" indicates water present at a temperature of at least about 374.2° C. and a pressure of at least about 22,100 kPa (about 221 bar), whether the water is pure water, or present as a mixture (e.g., water and ethanol, water and $CO_2$, etc.). Thus, for example, "a mixture of sub-critical water and supercritical carbon dioxide" indicates a mixture of water and carbon dioxide at a temperature and pressure above that of the critical point for carbon dioxide but below the critical point for water, regardless of whether the supercritical phase contains water and regardless of whether the water phase contains any carbon dioxide. For example, a mixture of sub-critical water and supercritical $CO_2$ may have a temperature of about 250° C. to about 280° C. and a pressure of at least about 22,500 kPa (about 225 bar).

The sub-, near-, or supercritical hydrolysis can be carried out at any suitable temperature (° C.), including, for example, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500. Each of the foregoing numbers can be preceded by the word "about," "at least about," or "less than about," and any of the foregoing numbers can be used singly to describe an open-ended range or in combination to describe a close-ended range. For example, the temperature can be at least about 120° C., about 360° C. to about 390° C., less than about 400° C., or about 360° C. to about 420° C.

The sub-, near-, or supercritical hydrolysis can be carried out at any suitable pressure (bar), including, for example, 1, 5, 10, 20, 30, 40, 50, 60, 70, 80, 90, 100, 110, 120, 125, 130, 140, 150, 160, 170, 175, 180, 190, 200, 210, 220, 225, 230, 240, 250, 260, 270, 275, 280, 290, 300, 310, 320, 325, 330, 340, 350, 360, 370, 380, 390, or 400. Each of the foregoing numbers can be preceded by the word "about," "at least about," or "less than about," and any of the foregoing numbers can be used singly to describe an open-ended range or in combination to describe a close-ended range. For example, the pressure can be at least about 20 bar, about 70 bar to about 275 bar, or less than about 250 bar. In some embodiments, the pressure is sufficient to maintain the fluid in liquid form. In some embodiments, the pressure is sufficient to maintain the fluid in supercritical form.

The sub-, near-, or supercritical hydrolysis can be carried out for any suitable residence time (seconds), including, for example, 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.5, 3, 3.5, 4, 4.5, 5, 6, 7, 8, 9, 10, 20, 30, 40, 50, or 60. Each of the foregoing numbers can be preceded by the word "about," "at least about," or "less than about," and any of the foregoing numbers can be used singly to describe an open-ended range or in combination to describe a close-ended range. In some embodiments, the residence time (min) can be 2, 4, 6, 8, 10, 20, 30, 40, 50, 60, 70, 80, 90, 100, 110, 120, 130, 140, 150, 160, 170, 180, 190, 200, 220, 240, 260, 280, or 300. Each of the foregoing numbers can be preceded by the word "about," "at least about," or "less than about," and any of the foregoing numbers (from either of the above lists) can be used singly to describe an open-ended range or in combination to describe a close-ended range. For example, the residence time can be at least about 0.1 sec, about 0.5 sec to about 2 sec, less than about 90 min, about 0.3 sec to about 1.5 sec, about 1 sec to about 3.5 min, or about 60 min to about 150 min.

Alternatively, or in addition, the original oligosaccharide composition is a product from the hemihydrolysis of a composition comprising cellulose and hemicellulose. The composition comprising cellulose and hemicellulose can be a biomass feedstock, as described herein. The hemihydrolysis step typically will include contacting the biomass feedstock comprising at least cellulose and hemicellulose with water, heat, and optionally acid to hydrolyze the hemicellulose (and starch, if present), which is then separated from the solids (e.g., cellulose and optionally other solids, such as lignin) as an original oligosaccharide composition comprising a first oligosaccharide. The remaining composition containing the solid cellulose and optionally other solids can, if desired, be subjected to a further hydrolysis reaction, such as a near-critical or supercritical hydrolysis, as described herein, to form another original oligosaccharide composition comprising a first oligosaccharide which also may be forwarded to the acid hydrolysis (in vessel 101), either separately, or together with other oligosaccharide compositions (e.g., the oligosaccharides from the hydrolysis of hemicellulose).

Some embodiments disclosed herein are set forth in the following clauses, and any combination of these clauses (or portions thereof) may be made to define an embodiment.

(1) A method comprising (a) providing a hydrolysis composition of at least 20 wt % of sugar equivalents, wherein the hydrolysis composition comprises a first oligosaccharide, water, optionally a soluble aromatic compound, and optionally organic and/or inorganic impurities, (b) contacting the hydrolysis composition with a catalyst in a first reactor to hydrolyze at least a portion of the first oligosaccharide to form a first product composition comprising a first monosaccharide and a second oligosaccharide, (c) separating the first monosaccharide from the first product composition to form a second product composition comprising the second oligosaccharide, wherein at least a portion of the second oligosaccharide is a reversion sugar, and (d) converting via a further hydrolysis step at least a portion of the second oligosaccharide to form a third product composition comprising a second monosaccharide.

(2) The method of embodiment (1), wherein the further hydrolysis step in step (d) comprises: (e) recycling at least a portion of the second oligosaccharide back to the first reactor, and (f) repeating step (b) using the portion of the second oligosaccharide as at least a portion of the first oligosaccharide.

(3) The method of embodiment (1), wherein the further hydrolysis step in step (d) comprises: (e) recycling at least a portion of the second oligosaccharide back to the first reactor, and (f) repeating steps (b)-(d) using the portion of the second oligosaccharide as at least a portion of the first oligosaccharide.

(4) The method of embodiment (1), wherein the further hydrolysis step in step (d) occurs in a second reactor.

(5) The method of embodiment (4), wherein the second reactor is different from the first reactor.

(6) The method of any one of embodiments (2)-(5), wherein the catalyst is an acid and the method further comprises adjusting the pH of the third product composition with a base.

(7) The method of embodiment (6), wherein the base is a precipitating base.

(8) The method of embodiment (1), further comprising, prior to step (d): (e) increasing the pH of the second product composition to form a pH-adjusted second product composition, and (f) concentrating the pH-adjusted second product composition to at least 20 wt % of sugar equivalents to form a concentrated pH-adjusted second product composition, and performing the converting step on the concentrated pH-adjusted second product composition in a second reactor.

(9) The method of embodiment (8), wherein the catalyst is an acid and wherein the pH of the second product composition is adjusted with a precipitating base.

(10) The method of any one of embodiments (6)-(9), wherein the pH of the third product composition, the pH of the second product composition, or both is adjusted to a pH of at least 2.5.

(11) The method of embodiment (7) or embodiment (9), wherein the precipitating base is CaO, $CaCO_3$, MgO, $Ca(OH)_2$, $NH_4OH$, or any combination thereof.

(12) The method of any one of embodiments (7), (9) or (11), further comprising removing solid by-product that is formed upon addition of the precipitating base.

(13) The method of embodiment (12), wherein the solid by-product is gypsum, $CaSO_4.2H_2O$.

(14) The method of embodiment (8) or embodiment (9), wherein the second reactor is the same as the first reactor.

(15) The method of any one of embodiments (1)-(14), further comprising combining the second monosaccharide with the first monosaccharide.

(16) The method of any one of embodiments (1)-(15), wherein the hydrolysis composition in step (a) is 30-90 wt % of sugar equivalents.

(17) The method of embodiment (16), wherein the hydrolysis composition in step (a) is 50-70 wt % of sugar equivalents.

(18) The method of any one of embodiments (1)-(17), wherein the catalyst is a mineral acid.

(19) The method of embodiment (18), wherein the mineral acid is sulfuric acid.

(20) The method of any one of embodiments (1)-(19), wherein at least 10 wt % of the first oligosaccharide is hydrolyzed to form the first monosaccharide.

(21) The method of any one of embodiments (1)-(20), wherein no more than 95 wt %, or no more than 85 wt %, of the first oligosaccharide is hydrolyzed in step (b) to form the first monosaccharide.

(22) The method of any one of embodiments (1)-(21), wherein the soluble aromatic compound is present in the hydrolysis composition, and wherein the method further comprises separating at least a portion of the soluble aromatic compound from the hydrolysis composition, the first product composition, the second product composition, the third product composition, or any combination thereof.

19

(23) The method of any one of embodiments (1)-(22), wherein the inorganic impurities are present in the hydrolysis composition, and wherein the method further comprises removing at least a portion of the inorganic impurities from the hydrolysis composition prior to step (b).

(24) The method of embodiment (23), wherein said inorganic impurities are removed using an ion exchange resin.

(25) The method of any one of embodiments (1)-(24), further comprising separating an organic acid, an aldehyde compound, or both that is/are present in the first product composition, before or after or concurrently with step (c).

(26) The method of embodiment (25), wherein the organic acid is levulinic acid, glycolic acid, acetic acid, formic acid, or lactic acid, or any combination thereof, and the aldehyde compound is furfural, hydroxymethylfurfural (HMF), glyceraldehyde, glycolaldehyde, syringaldehyde, homosyringaldehyde, coniferaldehyde, benzaldehyde, substituted benzaldehyde, vanillin, homovanillin, 4-hydroxy-3-methoxycinnamaldehyde, sinapaldehyde, or acetaldehyde, or any combination thereof.

(27) The method of embodiment (25) or (26), wherein separating the organic acid, aldehyde compound, or both employs chromatography, ion exchange, a membrane, electrodialysis, or any combination thereof.

(28) The method of any one of embodiments (1)-(27), wherein the separating in step (c) employs chromatography, a membrane, fermentation, or any combination thereof.

(29) The method of any one of embodiments (1)-(28), further comprising removing unreacted acid using chromatography heat, or a combination thereof.

(30) The method of any one of embodiments (27)-(29), wherein the separating employs chromatography, and the chromatography is simulated moving bed chromatography.

(31) The method of embodiment (30), wherein the simulated moving bed chromatography separates at least two streams from the first product composition, wherein the at least two streams comprise i) a stream comprising the first monosaccharide, and ii) a stream comprising the second oligosaccharides.

(32) The method of embodiment (31), wherein the simulated moving bed chromatography separates a third stream from the first product composition, wherein the third stream comprises organic impurities.

(33) The method of embodiment (28), wherein the first monosaccharide is separated in step (c) using fermentation by contacting the first product composition with at least one microorganism to form at least one fermentation product.

(34) The method of embodiment (33), wherein the at least one fermentation product comprises ethanol, butanol, or a farnesene compound, or any combination thereof.

(35) The method of any one of embodiments (1)-(34), wherein the first oligosaccharide is derived from hydrolysis of a feedstock comprising cellulose.

(36) The method of embodiment (35), wherein the hydrolysis comprises near-critical or supercritical hydrolysis.

(37) The method of any one of embodiments (1)-(36), wherein the first oligosaccharide is derived from hydrolysis of a feedstock comprising cellulose and hemicellulose.

(38) The method of any one of embodiments (1)-(37), wherein the reversion sugar is gentiobiose.

(39) The method of embodiment 38, wherein gentiobiose is present in the first product composition in an amount of at least 1 g/kg, based on the total weight of the first product composition.

(40) The method of any one of embodiments (1)-(37), wherein the reversion sugar is xylobiose.

20

(41) The method of any one of embodiments (1)-(37), wherein the reversion sugar has a bonding linkage that is not present in the original biomass.

The following examples further illustrate embodiments of the methods disclosed herein, but, of course, should not be construed as in any way limiting the scope of the methods.

EXAMPLES

Example 1

This example demonstrates the increasing formation of reversion sugars when the acid hydrolysis is performed at higher concentrations of gluco-oligosaccharides.

Figure 5:
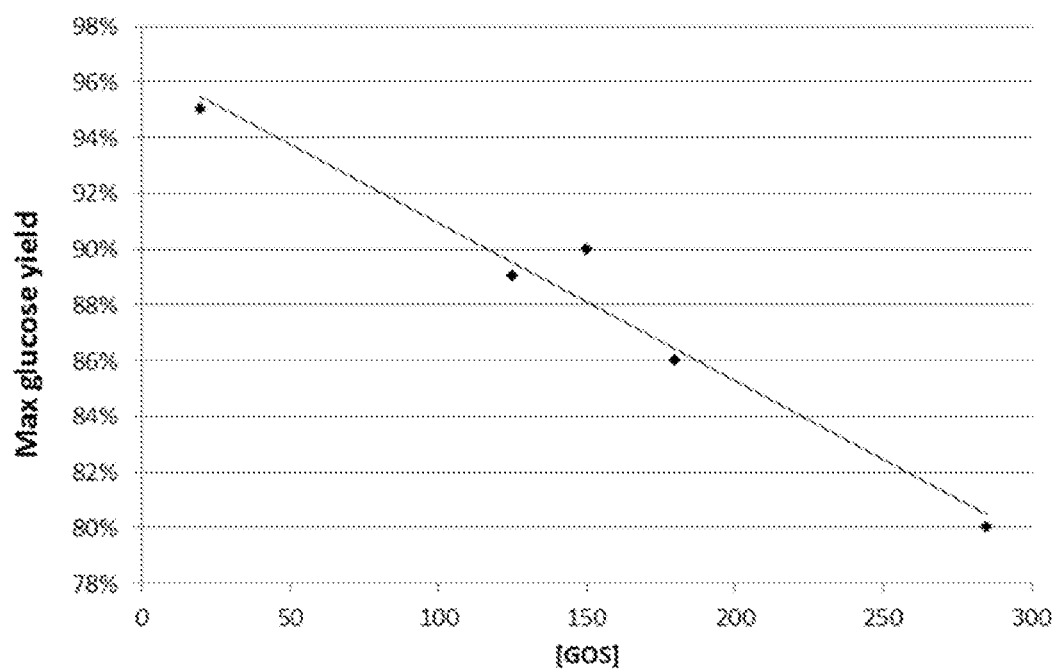
FIG. 5 shows a graph of maximum glucose yield as a function of gluco-oligosaccharide (GOS) concentration when the hydrolysis reaction is performed at various GOS concentrations.

The hydrolysis of gluco-oligosaccharides (GOS) was performed at varying concentrations of GOS. FIG. 5 shows that the maximum glucose yield decreases from as high as 95% yield obtained for hydrolysis of gluco-oligosaccharides at a concentration of 20 g/kg GOS to ~80% yield obtained for hydrolysis of gluco-oligosaccharides at a concentration of 285 g/kg GOS. The data in FIG. 5 were obtained for hydrolysis reactions of GOS performed at 120° C., pressure of ~2 atmospheres, and at a pH of approximately 1. However, additional data (not shown) has shown that the phenomenon is generalized and occurs over the temperature and pressure ranges disclosed herein, and that the pH only influences the rate of reaction (and hence reaction times) but not the maximum yield of glucose.

Figure 6:
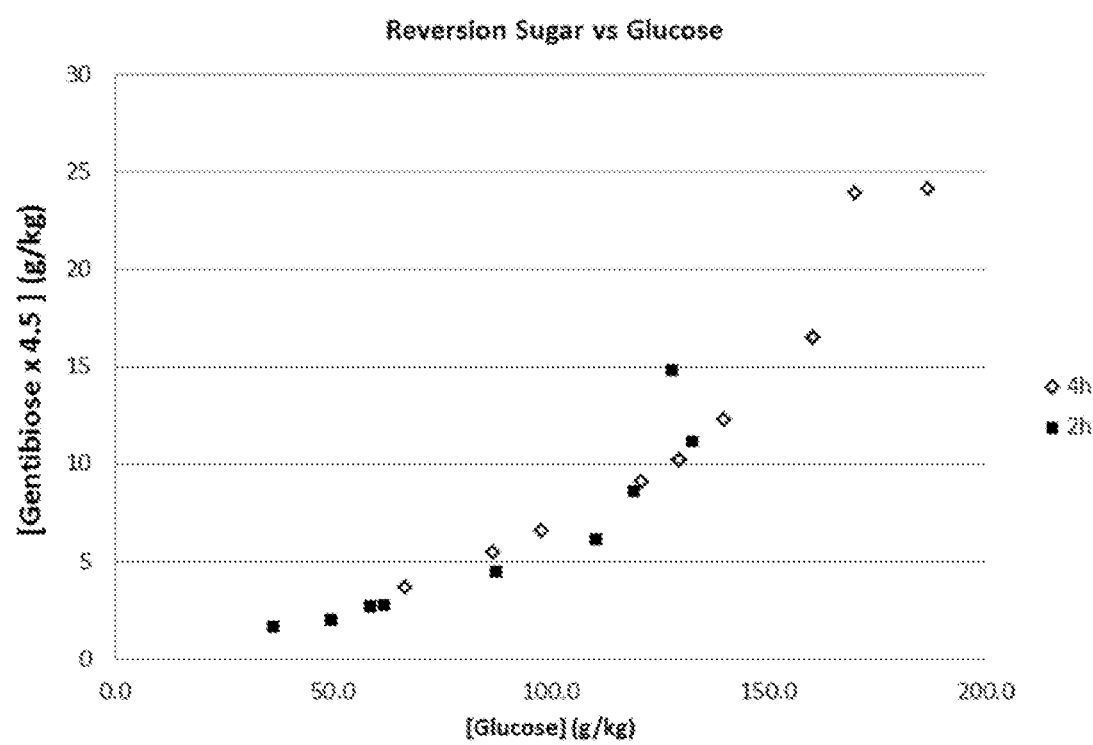
FIG. 6 shows a graph of concentration of reversion sugars with varying concentration of glucose formed from the hydrolysis reaction.

At the higher concentrations of GOS, the acid hydrolysis reaction produces higher concentrations of glucose, which in turn (under acid conditions) more readily combines into reversion sugars, particularly the disaccharide of glucose, such as gentiobiose. See, for example, FIG. 6: a plot of the concentration of gentiobiose as a function of the concentration of glucose. This by-product is not readily fermentable, and thus represents a yield loss in terms of glucose yield (unless recovered and/or recycled to a further hydrolysis step as described herein). In other words, FIGS. 5 and 6 show that higher concentrations of sugar equivalents in the hydrolysis reaction results in lower glucose yields due to the formation of reversion sugars.

Example 2

Figure 7A:
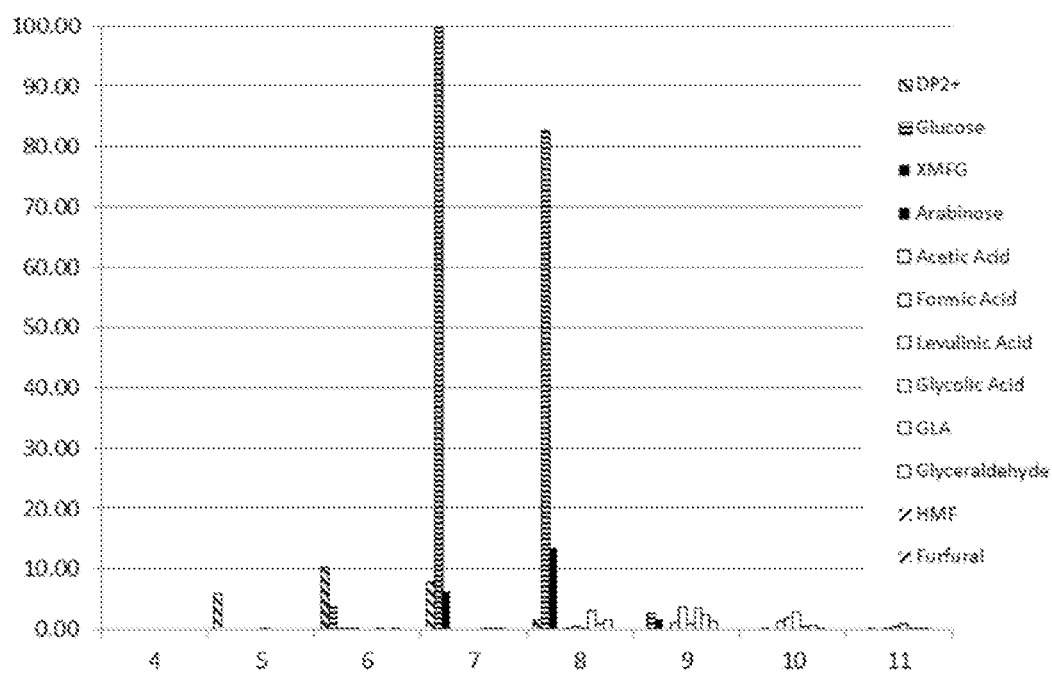
FIG. 7A shows the separation of the species obtained from the hydrolysis reaction of gluco-oligosaccharides by chromatography.
Figure 7B:
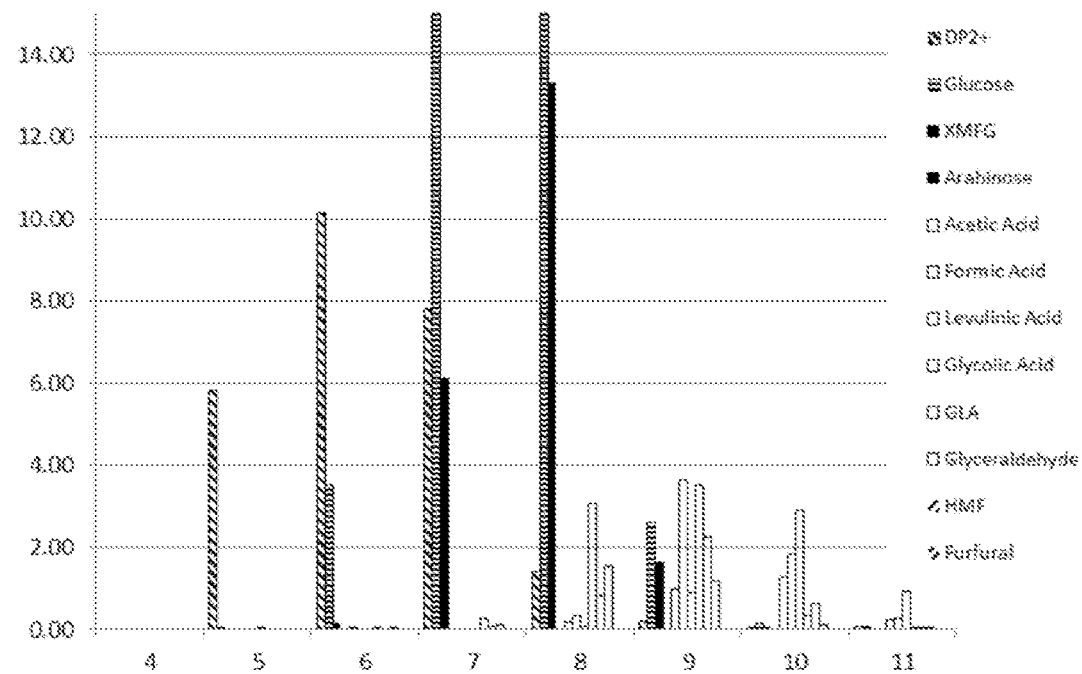
FIG. 7B is identical to FIG. 7A, except the y-axis scale runs from 0-15 to show detail near the baseline.

This example demonstrates the chromatographic separation of the species obtained from the hydrolysis reaction of gluco-oligosaccharides (FIGS. 7A and 7B). Note that FIGS. 7A and 7B are identical, except for the y-axis scale (to allow inspection of the data near the baseline). For the chromatography, three pulse tests were done using a jacketed glass chromatography column using deionized water as the eluent. For each trial, 15 mL of concentrated hydrolysis product was used. Samples were taken every 10 minutes for HPLC analysis. The x axis shows the sample numbers obtained in order (in 10 minute intervals), and thus is, effectively, an elution time showing that different species elute from the chromatography column over different time periods. Accordingly, different species can be separated into separate streams. For example, FIGS. 7A and 7B show that low DP oligomers (DP>2, if present) and the disaccharides (DP2), collectively referred to as DP2+, are eluted first (and, not shown, along with the sulfur-containing inorganic acids or ions derived therefrom); these are shown in elution samples 5 and 6, with some DP2+ extending into sample 7. Overall, FIG. 7 shows sample 5 is primarily DP2+ (and, not shown, sulfur-containing species, e.g., sulfuric acid), sample 6 has both DP2+ and glucose; sample 7 has some DP2+ and sugars (glucose+XMFG), sample 8 is primarily sugars (glucose+XMFG), and samples 9-11 are primarily organic acids. (XMFG is a peak that elutes with the appearance of a single entity, but is actually the combination of 4 species that elute together such that their peaks overlap—the four species are xylose, mannose, fructose, and galactose). Although this example shows a single pass on a small scale chromatography column, the separation may also be performed on a larger scale, and more effectively, using a Simulated Moving Bed (SMB) chromatography apparatus as described herein.

Example 3

This example demonstrates a hypothetical example of hydrolyzing an oligosaccharide-containing composition using the methods described herein.

A composition comprising gluco oligosaccharides, ash, and lignin having a content of about 5-10 wt % of sugar equivalents is provided in a vessel. Water is evaporated to concentrate the composition to about 60 wt % of sugar equivalents. The concentrated composition is passed through an ion exchange resin to remove ash from the composition. The de-ashed concentrated composition is then contacted with sulfuric acid to achieve a 0.5% acid concentration (pH of about 1.2) and to hydrolyze the gluco oligosaccharides in a first reactor. The hydrolysis reaction is stopped before complete hydrolysis of the gluco oligosaccharides to provide a first product composition comprising first monosaccharide (e.g., glucose), second gluco oligosaccharides, lignin, organic acid, aldehyde compounds, and acid. Under the acidic conditions, at least a portion of the lignin and humins precipitate from the composition, and are then filtered from the composition.

Using simulated moving bed (SMB) chromatography, and water as the eluent, the first monosaccharide (e.g., glucose) is separated from the first product composition. Water is removed from the first monosaccharide, and the concentrated monosaccharide (e.g., glucose, 30-60% solids) is stored for future use. Organic acids, aldehyde compounds, and other waste compounds are removed as a separate stream from the SMB. The remaining second product composition comprising the second gluco oligosaccharides (e.g., degree of polymerization of 2 or more), including reversion sugar and inorganic ions, with a solids content of about 20-25 wt % of sugar equivalents, is isolated as a separate stream.

At this point, the second product composition can be recycled back to the first reactor, and combined with the original oligosaccharide composition to form a combined composition with about 40 wt % of sugar equivalents. Additional acid can be added, if necessary, to further hydrolyze the second oligosaccharides.

In a first alternative embodiment, the second oligosaccharide is further hydrolyzed by the acid that is present in the second product composition in a second reactor. After the reaction has completed, lime (CaO) is added to raise the pH to at least 2.5 and precipitate gypsum ($CaSO_4 \cdot 2H_2O$). The gypsum is removed by filtration, and the resulting monosaccharide (e.g., glucose) is stored for further use or combined with the first monosaccharide produced.

In a second alternative embodiment, lime (CaO) is added to the second product composition to raise the pH to about 3 to provide a pH-adjusted second product composition and to precipitate gypsum ($CaSO_4 \cdot 2H_2O$). The gypsum is removed by filtration, and the remaining second gluco oligosaccharides in the pH-adjusted second product composition is combined with the original gluco oligosaccharide composition (comprising the first oligosaccharide) and subjected to further hydrolysis in the first reactor.

The hydrolysis of oligosaccharides to monosaccharides, as conventionally performed, is constrained to operate using a relatively low amount of sugar equivalents in the hydrolysis reaction (usually around 15 wt % sugar equivalents) in order to minimize yield loss to reversion sugars. The methods described herein provide a partial hydrolysis of oligosaccharides so that the dwell time of the monosaccharides is reduced, which minimizes further reaction of the monosaccharides to unwanted degradation products (which represent a yield loss). Furthermore, the monosaccharides are separated more quickly from the acids and the oligosaccharides, thereby minimizing the opportunity for the (acid-catalyzed) back reaction of monosaccharides to form reversion sugars (predominantly disaccharides, with a minor component of trisaccharides). Any partially reacted oligosaccharides (low DP oligosaccharides) and any reversion sugars formed are recycled either to the first hydrolysis reactor or to another hydrolysis reactor in order to convert to monosaccharides (which, again, are immediately separated from acids and oligosaccharides and collected as the pure monosaccharide). Because any yield loss to the formation of reversion sugars is only a temporary loss, which is recovered in the recycle process, the hydrolysis reaction of oligosaccharides to monosaccharides can operate at much higher concentrations of sugar equivalents (e.g. around 60 wt % of sugar equivalents), and is only limited, from practical considerations, by the viscosity of the compositions. The use of a simulated moving bed chromatography apparatus (or other suitable separation apparatus, including those described herein) enables the simultaneous separation of multiple species used or formed in the hydrolysis reaction allowing separate processing for at least three separated streams, including the pure product component (monosaccharides), waste products (organic acids and aldehydes and other organic waste species), as well as a recycle stream comprising oligosaccharides (including reversion sugars), catalyst (such as the mineral acid), and other inorganic impurities. The advantages of the methods described herein include higher monosaccharide yields resulting from minimizing reversion sugars and recycling them to form more monosaccharide, and lower costs resulting from operating at higher concentrations (which, for acid-catalyzed hydrolysis, requires less acid catalyst, less neutralizing base, and produces less solid gypsum for disposal).

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:
1. A method comprising
(a) providing a hydrolysis composition of at least 20% of sugar equivalents, wherein the hydrolysis composition comprises a first oligosaccharide, water, optionally a soluble aromatic compound, and optionally organic and/or inorganic impurities, (b) contacting the hydrolysis composition with a catalyst in a first reactor to hydrolyze at least a portion of the first oligosaccharide to form a first product composition comprising a first monosaccharide and a second oligosaccharide, (c) separating the first monosaccharide from the first product composition to form a second product composition comprising the second oligosaccharide, wherein at least a portion of the second oligosaccharide is a reversion sugar, and (d) converting via a further hydrolysis step at least a portion of the second oligosaccharide to form a third product composition comprising a second monosaccharide, wherein the further hydrolysis step in step (d) occurs in a second reactor, and wherein the second reactor is different from the first reactor.

2. A method comprising (a) providing a hydrolysis composition of at least 20% of sugar equivalents, wherein the hydrolysis composition comprises a first oligosaccharide, water, optionally a soluble aromatic compound, and optionally organic and/or inorganic impurities, (b) contacting the hydrolysis composition with a catalyst in a first reactor to hydrolyze at least a portion of the first oligosaccharide to form a first product composition comprising a first monosaccharide and a second oligosaccharide, (c) separating the first monosaccharide from the first product composition to form a second product composition comprising the second oligosaccharide, wherein at least a portion of the second oligosaccharide is a reversion sugar, (d) converting via a further hydrolysis step at least a portion of the second oligosaccharide to form a third product composition comprising a second monosaccharide, (e) recycling at least a portion of the second oligosaccharide back to the first reactor, and (f) repeating step (b) using the portion of the second oligosaccharide as at least a portion of the first oligosaccharide, wherein the catalyst is an acid and the method further comprises adjusting the pH of the third product composition with a base.

3. The method according to claim 2, wherein the catalyst is a mineral acid.

4. The method according to any of claims 1, 2 or 3, wherein the soluble aromatic compound is present in the hydrolysis composition, and wherein the method further comprises separating at least a portion of the soluble aromatic compound from the hydrolysis composition, the first product composition, the second product composition, the third product composition, or any combination thereof.

5. The method according to any of claim 1, or 2 to 4, further comprising separating an organic acid, and aldehyde compound, or both that is/are present in the first product composition before or after or concurrently with step (c).

6. The method according to any of claim 1, or 2 to 5, wherein the first oligosaccharide is derived from hydrolysis of a feedstock comprising cellulose, and wherein the hydrolysis comprises near-critical or super critical hydrolysis.

* * * * *